United States Patent [19]

Szkrybalo

[11] 3,931,149

[45] Jan. 6, 1976

[54] COPPER COMPLEXES OF DIISOPROPYLIDENE XYLO-2-HEXULOFURANOSONATE COMPOUNDS

[75] Inventor: William Szkrybalo, Verona, N.J.

[73] Assignee: Hoffmann-La Roche Inc., Nutley, N.J.

[22] Filed: Aug. 16, 1974

[21] Appl. No.: 497,994

[52] U.S. Cl................... 260/210 R; 71/75; 71/76; 71/77; 71/78; 71/88
[51] Int. Cl.[2]................................... C07H 17/04
[58] Field of Search................... 260/210 R, 340.7

[56] References Cited
UNITED STATES PATENTS

| | | |
|---|---|---|
| 3,451,993 | 6/1969 | Goshima et al................. 260/210 R |
| 3,542,761 | 11/1970 | Rossi............................... 260/210 R |
| 3,586,650 | 6/1971 | Gibbons et al.................. 260/210 R |
| 3,592,808 | 7/1971 | Theander......................... 260/210 R |
| 3,598,804 | 8/1971 | Hindley et al................... 260/210 R |

*Primary Examiner*—Johnnie R. Brown
*Attorney, Agent, or Firm*—Samuel L. Welt; Jon S. Saxe; William M. Farley

[57] ABSTRACT

Plant growth regulant compositions containing as the active ingredients copper (II) complexes of 2,3:4,6-di-O-(substituted)-alpha-L-xylo-2-hexulofuranosonic acid and, preferably, copper (II) 2,3:4,6-di-O-isopropylidene-alpha-L-xylo-2-hexulofuranosonate monohydrate and tripyridine copper (II) 2,3:4,6-di-O-isopropylidene-alpha-L-xylo-2-hexulofuranosonate, are described.

7 Claims, No Drawings

COPPER COMPLEXES OF DIISOPROPYLIDENE XYLO-2-HEXULOFURANOSONATE COMPOUNDS

SUMMARY OF THE INVENTION

This invention relates to plant growth regulating and herbicidal compositions as well as methods for controlling plant growth, utilizing as the active ingredient, a copper (II) complex of 2,3:4,6-di-O-(substituted)-alpha-L-xylo-2-hexulofuranosonic acid.

The compounds which are the active ingredients of these plant growth regulating compositions are particularly efficacious as abscission agents.

DETAILED DESCRIPTION OF THE INVENTION

This invention relates to plant growth regulant compositions and methods of using them. More particularly, this invention relates to plant growth regulant compositions containing compounds represented by the formula:

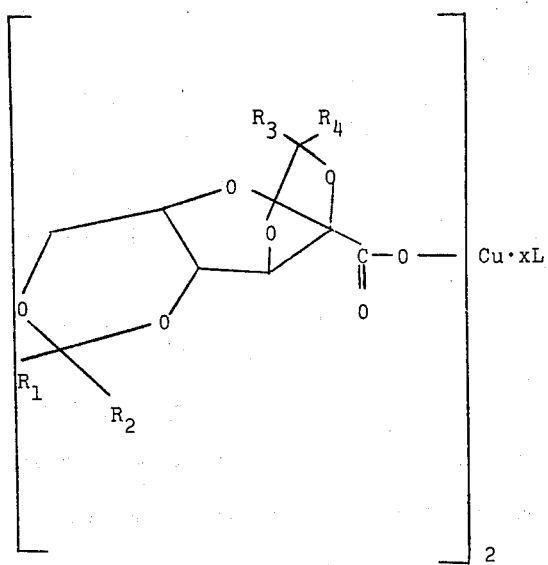

I wherein, at least one of $R_1$ and $R_2$ is methyl, ethyl or trifluoromethyl and the other of $R_1$ and $R_2$ is hydrogen, methyl, ethyl, propyl, isopropyl or trifluoromethyl, $R_3$ and $R_4$ are hydrogen, straight or branched chain aliphatic lower hydrocarbyl, aryl or $R_3$ and $R_4$ together are each a saturated ring containing from 3 to 8 carbon atoms, L is a ligand or group of ligands which are known to complex with copper and $x$ is an integer from 0 to 6, enantiomers and racemic mixtures.

The compounds which are the preferred active ingredients in the plant growth regulant compositions of this invention are represented by the formula

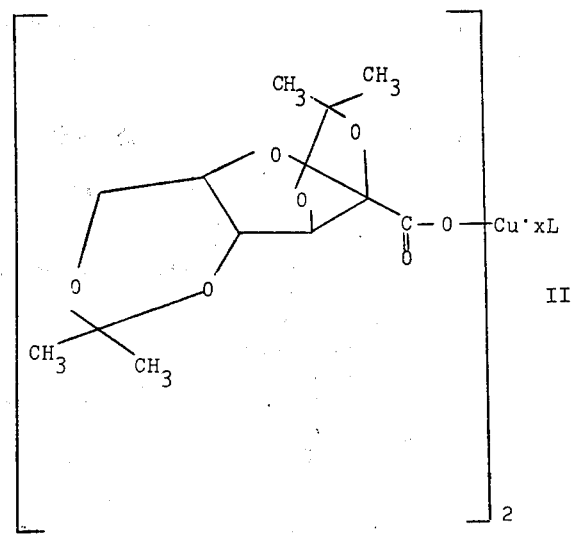

II wherein $x$ and L are described in Formula I, enantiomers and racemic mixtures.

A ligand is a group, ion or molecule coordinated to the central atom in a coordination complex.

Addition to these ligand group or groups tends to stabilize the resulting molecule. The ligand groups can also change the solubility characteristics of the resulting molecules and, thus, facilitate formulation and application of the compound.

Further, these ligands can be selected from compounds which have plant growth regulant activity, e.g., either herbicidal or abscission activity. Examples of such possible ligands include imidazoles, triazoles and aliphatic amines. Thus, the ligands could contribute to the overall plant growth regulant activity.

An extensive series of cupric complexes of carboxylic acids are known and it is believed, based on the structural similarity of, e.g., the acetate and the benzoate molecule to the 2,3:4,6-di-O-isopropylidene-alpha-L-xylo-2-hexulfuranosonic acid (DAG) molecule, that the cupric complexes with the various analogs of DAG have similar structures.

Thus, there are many ligands which form adducts with cupric II salts of 2,3:4,6-di-O-(substituted)-alpha-L-xylo-2-hexulofuranosonate. The ligands are, of course, molecular entities of the solvent.

Examples of ligands which form adducts with DAG-type compounds include the following.

A. Donor Atom-Nitrogen
   Examples in this group include
   i. Aliphatic amines such as triethylenediamine, N,N,N',N'-tetramethylethylenediamine,
   ii. Aryl amines such as aniline and m or p-toluidine and
   iii. Heterocyclics such as pyridine, α-, β- or γ-picoline, 2,2'-dipyridyl, 2-chloropyridine, 3,5-dimethylpyridine, quinoline, β-naphthoquinoline, pyrazine, quinoxaline and imidazole.
B. Donor Atom-Oxygen
   Examples in this group include
   i. Water;
   ii. Alcohols such as ethanol and butanol;
   iii. Ethers such as dioxane;

iv. Acids such as benzoic acid and
v. Group V oxides such as pyridine-N-oxide, quinoline-N-oxide, triphenylphosphine oxide, and triphenylarsine oxide.

C. Donor Atom-Phosphorous
An example from this group is triphenylphosphine.

D. Donor Atom-Indefinite
Examples from this group include dimethyl formamide and urea.

E. Donor Atom-Anionic
Examples from this group include thiocyano ion (NCS$^-$), nitro ion and bromo ion.

Preferred compounds represented by Formula II are:

Copper (II) 2,3:4,6-di-O-isopropylidene-alpha-L-xylo-2-hexulofuranosonate hydrate, Tripyridine copper (II) 2,3:4,6-di-O-isopropylidene-alpha-L-xylo-2-hexulofuranosonate, Diimidazole copper (II) 2,3:4,6-di-O-isopropylidene-alpha-L-xylo-2-hexulofuranosonate, and 2,2'-dipyridyl copper (II) 2,3:4,6-di-O-isopropylidene-alpha-L-xylo-2-hexulofuranosonate hydrate.

The compounds represented by formulas I and II are all of the L configuration since they are derived from the naturally occurring ketohexose, L-sorbose. While L-sorbose is the only known naturally occurring form of sorbose, its enantiomer, D-sorbose, can be synthesized. Compounds with the D-configuration and racemic mixtures of the compounds can be made using either D-sorbose or a mixture of D- and L-sorbose in identical preparatory procedures as for the L-configuration as discussed hereinafter.

All structural formulas set forth herein are for convenience only and are not intended to depict any absolute configuration. The formulas cover enantiomers and racemic mixtures. The Examples and other description, unless specifically noted otherwise, are directed to the racemic compounds.

As noted herein, the term "straight or branched chain aliphatic hydrocarbyl" denotes a monovalent substituent having from 1 to 20 carbon atoms consisting solely of carbon and hydrogen and which contains no aromatic unsaturation but which can be otherwise saturated or unsaturated, i.e., alkyl, alkenyl or alkynly group. As applied to these groups, the term "lower" denotes a group having a carbon skeleton containing from one to seven carbon atoms inclusive. The term "aryl" refers to an aromatic hydrocarbon such as phenyl and phenyl radicals having one or more alkyl, alkenyl, alkynyl, alkoxy or halo-lower alkoxy substituents thereon.

As used herein, "plant growth regulant" means a compound or compositions which affects the maturation and metabolism of plants. Hence, a plant growth regulant has many effects on plant growth. However, not all plant growth regulant active compounds affect plants the same way. For example, they could affect vegetative growth by retarding or stimulating terminal growth, and/or stimulating side branching and could inhibit new growth such as the development of new sprouts of woody plants, the sprouting of tubers and rhizomes and the development of sucker growth. Such regulants could affect flowering plangs by eliminating early flowering, by thinning of blossoms or by increasing the number of flowers. Fruit-bearing trees and bushes could be affected by increases in the number, size and quantity of the fruit, by producing seedless fruit, by accelerating senescence and fruit ripening and by stimulating fruit and/or leaf abscission. Both flowering and fruit plants could be affected by accelerating plant dormancy and maintaining bud dormancy. A plant growth regulant could cause selective post-emergent control of weeds by reducing their vigor and competitiveness and, thus, prevent their spread and stop normal seeding.

Some specific applictions of plant growth regulants include
preventing lodging of cereals;
increasing production of harvestable tea leaves by promoting side branching;
inhibiting sprouting of potatoes and onions in storage;
suppressing growth of grass, trees, shrubs, and other vegetation in decorative lawn areas, parks, golf courses and along highways and other rights-of-way;
accelarating fruit ripening and thus, aiding mechanical harvesting by a single or reduced number of pickings;
defoliating cotton to permit mechanical harvest;
inhibiting new growth of defoliated cotton and, thus, reducing staining of fiber during mechanical harvesting;
increasing the quality of the harvested crop, e.g., sugar content of sugar cane, sugarbeets, grapefruit, grapes, and other fruits;
aiding mechanical harvesting of nut crops by accelerating ripening, stimulating husk cracking and promoting abscission;
protecting crops from drought;
protecting fruit crops from frost by stimulating early dormancy and/or preventing premature breaking of dormancy;
increasing latex flow of rubber;
increasing frost resistance of winter cereals;
reducing the flowering or bolting of lettuce, sugar beets and tobacco;
controlling tobacco suckering;
stimulating increased fruit set of soybeans, peanuts, cotton, tomatoes, melons, and other fruits and enhancing fruit color and quality;
stimulating branching of pot plants, e.g. heather, azalea, chrysanthemum and geranium;
growth retardation in pot plants, e.g. poinsetta, petunia and chrysanthemum;
stimulating branching of young fruit trees, e.g. apple and pear.

In the control of grasses, particularly home lawns and industrial turfs, e.g. golf courses, it has been established that a maximum growth retardation as evidenced by diminished grass height as compared to an untreated control of about 40%–60% is desirable with about 50% growth retardation preferred. Any retardation less than 40% is ineffective in that grass control is not substantial enough to have a significant aesthetic effect and to reduce or eliminate manual care. On the other hand, retardation greater than 60% results in an undesired skimpy appearance to the lawn or turf with subsequent invasion thereof by weeds and other undesirable plants.

The active compounds show herbicidal activity especially against composite weeds, e.g., matricaria species and other weeds such as *papaver rhoeas, stellaria media* and *caprella bursa pastoris*.

The active compounds useful in this invention are particularly active against the following plants:

a. grasses such as *Agropyron repens, Bromus inermis, Bromus erectus, Deschampsia flexuosa, Alopecurus pratensis, Arrhenatherum elatius, Dactylis glomerata, Festuca pratensis, Trisetum flavescens, Holcus lanatus,*

*Lolium perenne, Poa annua, Poa neumoralis, Festuca ovina, Festuca rubra, Festuca nigrescens, Cynosurus cristatus, Agrostis schraderiana, Agrosti stolonifera, Phleum pratense, Phleum nodosum. Cynodon dactylon,* sugar cane and cereals such as corn, rice, wheat, rye barley, oats and sorghum;

b. trees and shrubs such as fruit trees, e.g., apple, pear, peach, cherry and citrus, as well as cocoa, tea, coffee, banana and rubber trees;

c. ornamental plants such as privet, horn-beam, white cedar, juniper, rose, azalea, chyrstanthemum, poinsethia, cyclamen, pyracantha, forsythia and magnolia;

d. field crops such as cotton soya beans, peanuts, tobacco and flax;

e. vegetables such as solanacease, e.g., tomatoes, legumes and cucumbers;

f. berries such as strawberries, blackberries, blueberries, cranberries, raspberries and currants.

In addition they are also useful for reducing pruning requirements in viticulture.

In order to effect uniform distribution of the active compound of the growth regulating compositions according to this invention, the compound can be mixed with conventional herbicidal adjuvants, modifiers, diluents, or conditioning agents so that they may be formulated as solutions, emulsions, dispersions, dusts or wettable powders.

Liquid formulations of the active compounds for direct spraying may be made, for example, as aqueous solutions containing a wetting agent such as 1% Tween or as solutions in solvent mixtures containing acetone, methanol and dimethyl formamide (DMF) in the ratio 90:8:2, volume/volume.

Emulsions can be prepared containing 25–50% of the active ingredient, and surface active agents, e.g., wetting agents, dispersing agents, emulsifying agents and the like, in sufficient amounts to impart the desired characteristics to the formulation.

The compounds can also be formulated as spray solutions from wettable powders using an inert diluent, e.g., kaolin. A typical spray solution formulated with a wettable powder, would, thus contain the active ingredient, from about 1% to about 5% of an inert diluent, minor amounts of dispering, wetting and antifoaming agents and, the balance, water.

Different forms of application may be better adapted to the various purposes for which the active compounds are to be used by the addition of substances which improve dispersion, adhesion, resistance to rain and penetrative power such as fatty acids, resins, wetting agents, emulsifying agents, glue and the like. In a similar manner, the biological spectrum may be broadened by the addition of substances having bactericial, herbicidal, and fungicidal properties and also by combination with fertilizers, chelating agents and other plant growth regulators.

Representative of herbicides and plant growth regulants which may be admixed with the compounds of this invention are:

2,2-dichloropropionic acid
N-(4-aminobenzenesulphonyl) methylcarbamate
2-chloro-4-ethylamino-6-isopropylamino-1,3,5-triazine
4-chloro-2-oxobezothiazolin-3-ylacetic acid
5-bromo-6-methyl-3-(1-methyl-n-propyl) uracil
3,5-dibromo-4-hydroxybenzonitrile
D-N-ethyl-2-(phenylcarbamoyloxy) propionamide
N-(4-bromo-3-chlorophenyl)-N'-methoxy-N'-methylurea
2-chloro-9-hydroxyfluorene-9-carboxylic acid
N'-4-(4-chlorophenoxy) phenyl -NN-dimethylurea
isopropyl N-(3-chlorophenyl) carbamate
2,3,5,6-tetrachloroterephthalic acid dimethyl ester (DCPA)
2,4-dichlorophenoxyacetic acid
4-isopropylamino-6-methylamino-2-methylthio-1,3,5-triazine
3,6-dichloro-2-methoxybenzoic acid
(±) 2-(2,4-dichlorophenoxy) propionic acid
9,10-dihydro-8a, 10a-diazoniaphenanthrene-2A
N'-(3,4-dichlorophenyl)-NN-dimethylurea
gibberellic acid
indolylacetic acid
indolybutyric acid
4-hydroxy-3,5-di-iodobenzonitrile
N'-(3,4-dichlorophenyl)-N-methoxy-N-methylurea
4-chloro-2-methylphenoxyacetic acid
4-(4-chloro-2-methylphenoxy) butyric acid
(±) 2-(4-chloro-2-methylphenoxy) propionic acid
N-(benzothiazol-2-yl)-NN'-dimethylurea
N'-(3-chloro-4-methoxyphenyl)-NN-dimethylurea
1,2,3,6-tetrahydro-3,6-dioxopyridazine
N'-(4-chlorophenyl)-N-methoxy-N-methylurea
N'-(4-chlorophenyl)-NN-dimethylurea
napthylacetic acid
N-1-naphthylphtalamic acid
2,4-dichlorophenyl 4-nitrophenyl ether
1,1'-dimethyl-4,4'-bipyridylium-2A
3-(m-toylcarbamoyloxy)phenyl carbamate
4-amino-3,5,6-trichloropicolinic acid
4,6bisisopropylamino-2-methylthio-1,3,5-triazine
N-(3,4-dichlorophenyl) propionamide
isopropyl N-phenylcarbamate
5-amino-4-chloro-2-phenylpyridazin-3(2H)-one
2-chloro-4,6-bisethylamino-1,3,5-triazine
sodium nonochloroacetate
2,4,5-trichlorophenoxyacetic acid
5-chloro-6-methyl-3-t-butyluracil
4-ethylamino-2-methylthio-6-t-butylamino-1,3,5-triazine(terbutryn)
2,3,5-triiodobenzoic acid
1,1,4-trimethyl-6-isopropyl-5-propionyl-indane Representative fungicides which may be admixed with the compounds of this invention are:

2,4-Dichloro-6-(o-chloroaniline)-S-triazine
2,4,5,6-Tetrachloroisophthalonitrile
p-Dimethylaminobenzenediazo sodium sulfonate
1,4-Dichloro-2,5-dimethoxybenzene
Manganous-ethylene-bisdithiocarbamate
Zinc-manganous-ethylene-bisdithiocarbamate
Coordination product of zinc and manganese-ethylene-bisdithiocarbamate
Methyl-1-(butylcarbamoyl)-2-benzoimidazol-carbamate
2-(4-thiazol)-benzimidazol
cis-N-[(trichloromethyl)-thio] -4-cyclohexene-1,2-dicarboximide Rates of application are based upon the results reported herein and are not to be deemed all-inclusive since many extraneous factors can alter the rates of application. For example, rates may vary not only among different plant species but also within a particular species depending on such factors as plant size and age, the compound used, the time of year, type of soil and such climatological conditions at application time as air temperature, rainfall and winds. In addition, if the compounds or compositions are applied via a soil drench, higher concentrations would be needed since this type of application is indirect in comparison to a direct application, upon leaves and stems, e.g. spraying.

The amount of active ingredient in the growth regulating compositions of this invention thus varies according to the plants to be controlled, the requisite application rate, type of application the active compound used and the control desired. Generally, the compositions contain less than 50% active compound.

Basically, the application rate of the active compound is that which is effective in providing the requisite growth regulant control to the plant. For example, as noted earlier an effective growth regulant amount for grasses is that amount which will retard grass height growth to 40%–60% of the normal growth rate. Hence, the choice of the minimum application rate would be determined by the minimum amount of active compound which is effective in regulating growth to the lowest limit of the desired growth retardation range. The choice of the maximum application rate would be determined as that amount which is effective in regulating growth to the upper limit of the desired growth retardation range, i.e., in the case of lawn and turf grasses, that amount above which a skimpy appearance to the turf or lawn results, or which prevents all subsequent growth.

With tomato plants, the criteria for effective growth retardant amount are different since a dwarfed, bushy plant wherein there is no loss of fruit quality or quantity is considered desirable. The parameters for effective growth regulant activity for such plants are retarded terminal growth and enhanced or non-retarded lateral growth as the minimum effects and retarded terminal and lateral growth as the maximum effects. Application rates of active compounds which have these desired effects on tomato plant growth are determined with these criteria in mind. In order to obtain the greatest post-emergent growth regulating activity, application rates of from 0.5 pound to 20 pounds or more per acre generally are needed based on the weight of the active compound. The greatest post-emergence growth regulating activity is normally obtained with application rates of from about 1 to 15 pounds or more of active ingredient per acre. A preferred dosage range in solutions for spray application is from 100 to 10,000 ppm depending on the species to be treated and the active compound utilized with the most preferred range generally being 100 to 1,000 ppm.

An additional advantage in the use of the active compounds of this invention is the absence of any permanent effect on plants or any regulant residue in the soil. As the compounds undergo slow decomposition, there is a consequent diminution of activity. Such an effect is advantageous in that
 a. a short-term effect, which can be lengthened by subsequent additional application, is attained;
 b. normal growth activity resumes as the regulant activity decreases; and
 c. no deleterious residues remain on the plants or in the soil.

The length of the retardant effect varies with the compound used and other factors such as the plant species, climatological conditions, etc.

As noted earlier, these plant growth regulating compositions are particulary efficacious as abscission agents. The emphasis on mechanical harvesting of tree-borne fruit has stimulated extensive investigation of chemicals which facilitate harvesting of such fruit by reducing the force of attachment between the fruit and the stem. To be efficacious, such chemicals, known as abscission agents, must reduce the force required to remove the fruit from the stem, aid in separating the complete stem from the fruit leaving a clean unbroken plug, cause a minimum of burning and pitting of the tree's fruit, delay rotting of the fruit after it is either picked or falls to the ground, have no deleterious effect on green fruit and have no appreciable detrimental effect on the leaves of treated plants. The ideal abscission agent is simple, inexpensive, amenable to simple application, e.g. by spraying, and compatible with aqueous and/or oily spray compositions. In addition to these requirements for efficacy, an abscission agent must be non-toxic to humans and/or animals when eaten and must meet government safety standards as a food additive or "residue".

It has been found that when a plant growth regulating composition containing a compound represented by Formulae I and II is applied to fruit-bearing trees the force required to remove the fruit from the stem is thereby significantly reduced in comparison to that required to remove the fruit from untreated trees. Further, fruit removed from trees with the aid of the abscission compositions of the present invention has been found to be relatively free from pitting and rotting.

For use as abscission agents, the compositions of the present invention can be applied to the fruit-bearing trees in liquid or powdered formulations. Application may be made to the roots, trunks, limbs, leaves or fruit. For example, the normal abscission composition according to the present invention can be dusted on the trees from airplanes or applied to the base of the trees in order to be absorbed by the roots. The preferred method of application and the most efficient is to apply the compositions in the form of an aqueous spray. If desired, an oily spray may be used. In the interest of economy, however, an aqueous spray is preferred.

In order to achieve the most efficient use of the normal abscission compositions of the present invention, it is preferred to apply them from about 1 to 2 weeks prior to harvesting of the fruit depending on the temperature. In areas where a rainfall is expected subsequent to application but prior to harvesting, a conventional sticking agent may be incorporated into the compositions. Typical examples of such sticking agents include glue, casein, salts of alginic acids, cellulose gums and their derivatives, polyvinyl pyrrolidone, vegetable gums, propylene glycol, invert syrup, corn syrup and the like.

Compositions of this invention when used for abscission contain as an essential active ingredient a compound represented by Formulas I and II. If desired, inert materials conventionally used in agriculture for application to trees may be utilized in conjunction with the active ingredients of the normal abscission compositions of the present invention. Such adjuvants include, for example, surface active agents, carriers, sticking agents, stabilizers and the like.

The concentration of the compounds represented by Formulas I and II suitable for use in the novel abscission compositions of the present invention vary, but, in order to be most effective, it is necessary that a sufficient amount be present to provide from about 0.05% to about 1.0% by weight of the active compound in an aqueous spray solution. This amount will naturally vary according to the fruit to be sprayed and the size of the tree or bush. The application rate is that which is effective in facilitating harvesting. For spray applications, the aqueous solution containing the abscission composition is applied to the tree until run-off. In commercial operations this involves the application of from 350 to 100 gallons of a dilute spray solution (0.5–1% by weight of active ingredient) per acre, depending upon the number and size of the trees sprayed.

In order to form the preferred liquid spray formulations embodying the abscission compositions of the present invention, the active ingredients or a salt thereof are dispersed in a carrier such as, for example, water. From about 0.1% to about 0.8% by weight, based on the weight of the carrier, of a surface active agent may be included in the liquid spray compositions. Typical surface active agents are Triton, R-1956, a water-dispersible, resin-based surfactant manufactured by Rohm and Haas and X-77 (Chevron Ortho) a nonionic type composition containing as the principal functioning agent alkylarylpolyoxyethylene glycols, free fatty acids and isopropanol.

The abscission compositions of this invention effectively abscind a variety of fruits from trees. Typical fruits with which these compositions are efficacious include oranges, grapefruits, olives, apples, cherries and the like. They are also efficacious in use with other crops such as cotton (to drop the leaves) and soybeans.

As has been stated, it is preferred to apply the novel abscission compositions of the present invention to fruit trees in the form of an aqueous spray.

Since oranges can be considered a typical fruit representative of those amenable to treatment by chemical abscission agents, the efficacy of the novel plant growth regulating compositions of the present invention as abscission agents may be illustrated with respect thereto.

For evaluation, the copper (II) 2,3:4,6-di-O-isopropylidene-alpha-L-xylo-2-hexulofuranosonate hydrate and the tripyridine copper (II) 2,3:4,6-di-O-isopropylidene-alpha-L-xylo-2-hexulofuranosonate were tested for their activity as abscission agents for citrus fruits, i.e., oranges. Aqueous solutions containing 0.4% and 0.2% by weight of the copper (II) salts and 0.5% of X-77 were prepared. These solutions were applied as a spray to valencia orange trees. Ten days after spraying, the pull force required to remove the oranges from the stem was measured and found to be significantly reduced. In addition, the estimate of the percent leaf drop was also acceptable.

A pull force of not more than 6 pounds is required to be commercially acceptable for mechanical harvesting.

Further, resulting leaf drop should not exceed 40% to avoid deleterious effects on fruit quantity with a range of 20%–30% being more desirable.

In addition to the abscission effect, the fruit also showed a marked enhancement in color, i.e., a much deeper and darker color than the untreated fruit.

The sugar content and/or total solids in the treated fruits also increased in comparison to the untreated fruit.

2,3:4,6-di-O-isopropylidene-alpha-L-xylo-2-hexulofuranosonic acid monohydrate (also known as 2,3:4,6-di-O-isopropylidene-2-keto-L-gulonic acid monohydrate) is a well-known chemical of commerce and is an intermediate in the synthetic preparation of L-ascorbic acid. It is prepared by the oxidation in alkaline or neutral media of diacetone-L-sorofuranose which is, in turn prepared from the reaction of L-sorbose with acetone in the presence of a strong acid.

The copper (II) salts of DAG are prepared by conventional processes. DAG is added with rapid stirring to cupric carbonate suspended in water at 0°–5°C. The mixture is stirred for 24 hours. The resulting product is evaporated to dryness under vacuum and recrystallized from acetone-hexane. The pyridine and substituted pyridine copper (II) salts are prepared by analogous procedures using pyridine or a substituted pyridine solvent.

Compounds in which the 4,6-O-isopropylidene group (i.e., $R_1$ and $R_2$ of Formula I) has been replaced are prepared by a ketal interchange reaction in which DAG is dissolved in the desired ketone, aldehyde, ketal or acetal using an acid catalyst.

Representative of the ketones and aldehydes which can be used in the preparatory procedure are those of the general formula

wherein $R_5$ can be, e.g., methyl, ethyl, lower alkyl, trifluoromethyl and $R_6$ can be, e.g., methyl, ethyl, trifluoromethyl or hydrogen. Typical compounds include diethyl ketone, methyl ethyl ketone, paraldehyde, di(trifluoromethyl) ketone and trifluoroacetaldehyde. Where an unsymmetrical aldehyde or ketone is used, the larger or bulkier group occupies the equatorial position to form a new asymmetric center.

Any strong acid can be used as the catalyst with perchloric acid the preferred catalyst. Other representative acids include sulfuric acid, hydrochloric acid, p-toluene sulfonic acid, methane sulfonic acid and trifluoromethane sulfonic acid.

A temperature range of from about −20°C. to about 50°C. can be used with a range of 20°C. −30°C. (room temperature) preferred. 100°C., near the decomposition point of DAG, is the limiting temperature.

The compounds in which both O-isopropylidene groups have been replaced are prepared from L-sorbose following the procedure described in Reichstein and Grussner, Helv. Chim. Acta, 17, 311 (1934). In brief, a suitable ketone or aldehyde is reacted with L-sorbose in the presence of a strong acid catalyst e.g., sulfuric acid, at room temperature or below. The intermediate which forms, 2.3:4,6-di-O-alkylidene-α-L-sorbofuranose, is subsequently oxidized in alkaline or neutral media.

In the preparation of the di-O-alkylidene sorbofuranose, the strong acid catalysts include sulfuric acid, perchloric acid, hydrochloric acid, p-toluene sulfonic acid and the like with sulfuric acid preferred.

Since the reaction is exothermic room temperature or below are used with the preferred temperature range being from about 0°C. to about −20°C.

In the subsequent preparation of the acid from the sorbofuranose intermediate, oxidation is carried out in alkaline or neutral media using such agents as $NaMnO_4$, $K_2Cr_2O_7$, $KMnO_4/KOH$ and $NaOCl/Ni^{++}$ with the latter two preferred. In addition, the oxidation can also be achieved catalytically using palladium or platinum and oxygen.

A temperature range of from room temperature to 100°C. can be used from a range from about 50°C. to about 60°C. preferred.

It will be appreciated, of course, that all of the compounds represented by Formulas I and II are not active against all plants. However, each of the active compounds within the scope of this invention has activity against a specific plant or plants which is a function of the compound.

The following Examples illustrate the invention.

EXAMPLE 1

Preparation of Copper (II) 2,3:4,6-di-O-isopropylidene-alpha-L-xylo-2-hexulofuranosonate hydrate 50 grams of cupric carbonate are suspended in 200 ml. of distilled water at 0°–5°C. 29.2 grams of 2,3:4,6-di-O-isopropylidene-alpha-L-xylo-2-hexulofuranosic acid hydrate are added slowly over a 6 hour period. The mixture is stirred for about 24 hours, filtered and the filtrate is concentrated to dryness under vacuum. The resulting green syrup crystallized on standing. This compound was then stirred with 50 ml. of a 1:1 acetone-hexane mixture and filtered. The purified product was analyzed as follows:

Calc. for $C_{24}H_{34}O_{14}CU.H_2O$: C, 45.89 H, 5.78 Cu, 10.1 $H_2O$, 2.87; Found: C, 45.48 H, 5.89 Cu, 9.84 $H_2O$, 3.33.

EXAMPLE 2

Preparation of Tripyridine copper (II) 2,3:4,6-di-O-isopropylidene-alpha-L-xylo-2-hexulofuransonate 50 grams of cupric carbonate were suspened in 200 ml. of pyridine. 29.2 grams of 2,3:4,6-di-O-isopropylidene-alpha-L-xylo-2-hexulofuranosonic acid hydrate were added slowly with stirring. Stirring was continued for 24 hours. The mixture was filtered and the filtrate was concentrated under vacuum. The crude deep-blue colored product was recrystallized from a 1:1 acetone-hexane mixture.

Calc. for $C_{24}H_{34}O_{14}Cu.(C_5H_5N)_3$: C, 55.28 H, 5.83 N, 4.96; Found: C, 55.53 H, 6.10 N, 4.65.

Example 3

Following the procedure described in Example 2 above, but using 4-methylpyridine as the solvent, di-(4-methylpyridine) copper (II) 2,3:4,6-di-O-isopropylidene-alpha-L-xylo-2-hexulofuranosonate was prepared.

Calc. for $C_{24}H_{34}O_{14}Cu.(C_6H_7N)_2$: C, 54.29 H, 6.08 N, 3.52 Cu, 7.98; Found: C, 54.20 H, 6.08 N, 3.52 Cu, 7.98.

EXAMPLE 4

Following the procedure described in Example 2 above, but using 2-methylpyridine as the solvent, di-(2-methylpyridine) copper (II) 2,3:4,6-di-O-isopropylidene-alpha-L-xylo-2-hexulofuranosonate was prepared.

Calc. for $C_{24}H_{34}O_{14}Cu.(C_6H_7N)_2$: C, 54.29 H, 6.08 N, 3.52 Cu 7.98; Found: C, 54.07 H, 5.89 N, 3.38 Cu 7.38.

EXAMPLE 5

Following the procedure described in Example 2 above, but using 3-methylpyridine as the solvent, tri-(3-methylpyridine) copper (II) 2,3:4,6-di-O-isopropylidene-alpha-L-xylo-2-hexulofuranosonate hydrate was prepared.

Calc. for $C_{24}H_{34}O_{14}Cu.(C_6H_7N)_3.H_2O$: C, 55.58 H, 6.32 N, 4.63 $H_2O$, 1.99; Found C, 55.44 H, 6.26 N, 4.53 $H_2O$, 1.77.

EXAMPLE 6

Preparation of Diimidazole copper (II) 2,3:4,6-di-O-isopropylidene-alpha-L-xylo-2-hexulofuranosonate hydrate 20 grams of cupric carbonate were suspended in 80 ml. of methyl alcohol and 6.8 grams of imidazole. 20.2 grams of 2,3:4,6-di-O-isopropylidene-alpha-L-xylo-2-hexulofuranosic acid hydrate are added slowly over a 6 hour period. The mixture is stirred for about 24 hours, at room temperature, filtered and evaporated to dryness.

Calc. for $C_{24}H_{34}O_{14}Cu.(C_3H_4N_2)_2.1/2\ H_2O$: C, 47.71, H, 5.74, N, 7.42, $H_2O$, 1.19; Found: C, 47.44, H, 5.73, N, 7.22, $H_2O$, 1.21.

EXAMPLE 7

Preparation of 2,2'-Dipyridyl copper (II) 2,3:4,6-di-O-isopropylidene-alpha-L-xylo-2-hexulofuranosonate hydrate 20 grams of cupric carbonate were suspened in 100 ml. of methyl alcohol and 7.8 grams of 2,2'-dipyridyl. 20.2 grams of 2,3:4,6-di-O-isopropylidene-alpha-L-xylo-2-hexulofuranosonic acid hydrate are added slowly over a 6 hour period. The mixture is stirred overnight at room temperature, filtered and evaporated to dryness under vacuum. The resulting blue compound was analyzed as follows:

Calc. for $C_{24}H_{34}O_{14}Cu.(C_5H_4N)_2 . H_2O$: C, 52.07, H, 5.65, N, 3.57, Cu, 8.10; Found: C, 51.82, H, 5.69, N, 3.69, Cu, 7.90.

EXAMPLE 8

The abscission activities of copper (II) 2,3:4,6-di-O-isopropylidene-alpha-L-xylo-2-hexulofuranosonate hydrate (Formulation A in Table I below) and tripyridine copper (II) 2,3:4,6-di-O-isopropylidene-alpha-L-xylo-2-hexulofuranosonate (Formulation B in Table I below) were evaluated on valencia oranges.

Each compound was dissolved in water form solutions containing 0.4% and 0.2% by weight of active ingredient. 0.5% by weight of X-77, a surface-active agent, was added to each solution. A control spray solution containing 10 ppm of cycloheximide was also prepared.

The solutions were applied to tree branches at a pressure of 30 psi. using a $CO_2$ sprayer equipped with a jet-set nozzle. Spraying was continued to run-off.

Ten days after spraying, ten fruit were clipped from each branch and a pull force gauge was used to measure the force need to remove the fruit from the stem.

The percent leaf drop was also estimated after 10 days.

Results are tabulated below.

Table I

| Pull Force and Leaf Drop of Valencia Oranges 10 days after Spray Application of Abscission Agents | | | |
|---|---|---|---|
| Formulation | Rate | Pull Force, Pounds | Leaf Drop, Percent |
| Untreated | — | 18.6 | 0 |
| Cycloheximide | 0.002% (20 ppm) | 0 | 95 |
| | 0.001% | | |

Table I-continued

Pull Force and Leaf Drop of Valencia Oranges 10 days after Spray Application of Abscission Agents

| Formulation | Rate | Pull Force, Pounds | Leaf Drop, Percent |
|---|---|---|---|
| Cycloheximide | (10 ppm) | 1.2 | 50 |
| A | 0.4% | 2.5 | 30 |
| A | 0.2% | 1.8 | 20 |
| B | 0.4% | 2.5 | 80 |
| B | 0.2% | 2.3 | 20 |
| DAG, sodium salt | 0.4% | 4.6 | 20 |
| DAG, soidum salt | 0.2% | 6.0 | 20 |

A - Copper (II) 2,3:4,6-di-O-isopropylidene-alpha-L-xylo-2-hexulofuranosonate hydrate.
B - Tripyridine copper (II) 2,3:4,6-di-O-isopropylidene-alpha-L-xylo-2-hexulofuranosonate.

I claim:
1. Copper (II) 2,3:4,6-di-O-isopropylidene-alpha-L-xylo-2-hexulofuranosonate hydrate.
2. Tripyridine copper (II) 2,3:4,6-di-O-isopropylidene-alpha-L-xylo-2-hexulofuranosonate.
3. Diimidazole copper (II) 2,3:4,6-di-O-isopropylidene-alpha-L-xylo-2-hexulofuranosonate hemihydrate.
4. 2,2'-dipyridyl copper (II) 2,3:4,6-di-O-isopropylidene-alpha-L-xylo-2-hexulofuranosonate hydrate.
5. Di-(4-methylpyridine) copper (II) 2,3:4,6-di-O-isopropylidene-alpha-L-xylo-2-hexulofuranosonate.
6. Di-(2-methylpyridine) copper (II) 2,3:4,6-di-O-isopropylidene-alpha-L-xylo-2-hexulofuranosonate.
7. Tri-(3-methylpyridine) copper (II) 2,3:4,6-di-O-isopropylidene-alpha-L-xylo-2-hexulofuranosonate hydrate.

* * * * *